US00PP11546P

United States Patent [19]

Boeder

[11] Patent Number: Plant 11,546

[45] Date of Patent: Oct. 3, 2000

[54] CHRYSANTHEMUM PLANT NAMED 'YELLOW ABOUT TIME'

[75] Inventor: Mark Boeder, West Wittering, United Kingdom

[73] Assignee: Cleangro Limited, West Sussex, United Kingdom

[21] Appl. No.: 09/133,899

[22] Filed: Aug. 13, 1998

[51] Int. Cl.[7] ..... A01H 5/00

[52] U.S. Cl. ..... Plt./289

[58] Field of Search ..... Plt./289

[56] References Cited

PUBLICATIONS

UPOV–ROM, 1999/02, Plant Variety Database, GTI Jouve Retrieval Software, citation for 'Yellow About Time' chrysanthemum.

*Primary Examiner*—Howard J. Locker
*Attorney, Agent, or Firm*—Christie, Parker & Hale, LLP

[57] ABSTRACT

A new variety of chrysanthemum producing bright yellow flowers with long, recurved outer ray florets.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Yellow About Time'.

The new variety was discovered as a natural single branch mutation of the variety 'Jewel Time' (unpatented). The new variety has been asexually reproduced by vegetative cuttings in Ventura County, Calif. and the distinguishing characteristics are retained through successive generations of asexual reproduction.

SUMMARY OF THE INVENTION

'Yellow About Time' is pot type chrysanthemum plant variety that produces bright yellow flowers with long, recurved outer ray florets.

COMPARISON WITH PARENT

Flowers of the new variety differ in color from its parent which produces creamy white flowers.

BRIEF DESCRIPTION OF ILLUSTRATION

The acompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'Yellow About Time' has not been observed under all possible environmental conditions, The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after plating and a second time to remove center bud just as buds are developing. It has been observed that the shelf life of 'Yellow About Time' is about 24 days with the response time of about 8 weeks. One treatment with growth regulator B9 at 2000 ppm is useful and was applied to the plants described herein. Desirable growing conditions include average night temperatures of about 18°–20° C., day temperatures of about 20°–30° C. and about 3,000–5,000 foot-candles of light. The new variety can be grown as a disbud or spray pot. The drawing shows the variety as a spray pot.

Plant:
- *Habit.*—Upright, spreading herbaceous.
- *Height.*—About 22 cm.
- *Number of breaks from pinch.*—About 3 to 4.
- *Length of lateral branches.*—About 18 cm.
- *Stem color.*—Near 138A.

Foliage:
- *Leaf arrangement.*—Alternate.
- *Number of leaves per lateral branch.*—About 13.
- *Leaf size.*—Length: About 7.2 cm. Width: About 4.5 cm.
- *Leaf shape.*—Obvate.
- *Attachment.*—Petioled.
- *Leaf apex.*—Acute.
- *Base.*—Truncate.
- *Margin.*—Cleft.
- *Aspect.*—Slightly revolute.
- *Surface.*—Top: Lightly pubescent. Bottom: Pubescent. Mid Vein Color: Underside: Near 137D. Upperside: Near 146C.
- *Petiole length.*—About 1.8 cm. Color: Near 146D.
- *Color.*—Mature leaf: Top: Near 147A. Bottom: Near 137C. Young leaf: Top: Near 137A. Bottom: Near 137D.

Bloom:
- *Inflorescence form.*—Cymeous cluster.
- *Bloom form.*—Decorative.
- *Number of blooms per branch.*—About 5.
- *Diameter of fully expanded bloom.*—About 10 cm.
- *Depth of fully expanded bloom.*—About 2.5 cm.
- *Sepal number.*—About 20.
- *Color.*—Near 137C.
- *Length.*—About 1.2 cm.
- *Peduncle.*—Length: Terminal: About 4.3 cm. Lateral: About 6.8 cm. Aspect: Strong, straight. Surface: Pubescent. Color: Near 138A.
- *Flower bud shape* (*when just showing color*).—Color: Near 4B. Diameter: About 1 cm. Height: About 0.9 cm. Shape: Slightly flattened sphere.
- *Ray florets.*—Number per flower: About 120. Texture: Matte. Shape: Oblancolate. Apex: 3 Obtuse, irregular lobes. Base: Tapered. Margin: Entire. Aspect: Outer ray florets recurved. Length: About 5.2 cm. Width: About 1.5 cm.

*Disc florets.*—Number per flower: About 5. Textures: Shiny. Shape: Cylindric. Length: About 0.3 cm. Width: About 0.07 cm.

*Fragrance.*—Very faint.

Flower color:

*General flower coloration.*—Clear yellow decorative.

*Ray florets, top side.*—Immature: Near 8B. Mature: Near 13C. Fading: Near 10A.

*Ray floret, under side.*—Immature: Near 12C. Mature: Near 8C. Fading: Near 8.

*Disc florets C.*—Immature: Near 154B. Mature: Near 154A. Fading: Near 2D.

*Changes as the flower ages.*—Color becomes lighter, outer ray florets become more recurved.

Reproductive organs:

*Ray florets.*—Pistillate. Stigma shape: 2 branched. Stigma color: About 6C. Style length: About 0.6 cm. Style color: Near 154D.

*Disc florets.*—Stigma shape: Linear. Stigma color: Near 13C. Style Length: About 0.15 cm. Style color: Near 6D. Stamen number: About 5. Anther length: About 0.15 cm. Pollen color: Near 16A. Pollen quantity: Minimal.

What is claimed is:

1. A new and distinct chrysanthemum plant of the variety substantially as herein shown and described.

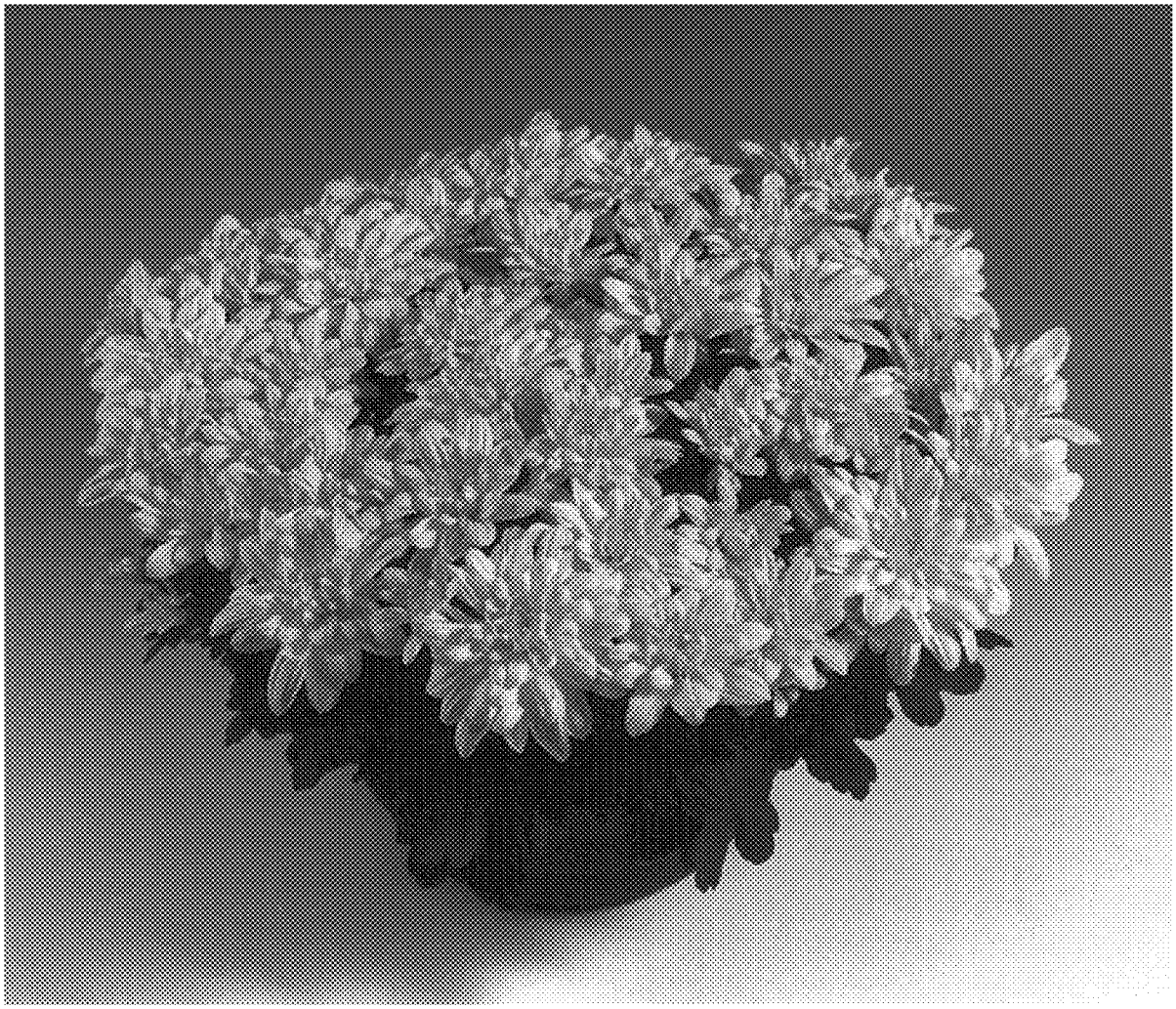

* * * * *